United States Patent [19]

Yoshida et al.

[11] Patent Number: 4,678,327

[45] Date of Patent: Jul. 7, 1987

[54] METHOD FOR INSPECTING AN OPTICAL FIBER

[75] Inventors: Noriyuki Yoshida; Kenichi Takahashi, both of Osaka, Japan

[73] Assignee: Sumitomo Electric Industries, Ltd., Osaka, Japan

[21] Appl. No.: 797,015

[22] Filed: Nov. 12, 1985

[30] Foreign Application Priority Data

Dec. 24, 1984 [JP] Japan .................. 59-279335

[51] Int. Cl.⁴ ............................................ G01N 21/89
[52] U.S. Cl. .................................................. 356/73.1
[58] Field of Search ......................................... 356/73.1

[56] References Cited

U.S. PATENT DOCUMENTS 4,021,217 5/1977 Bondybeh et al. ............ 356/73.1 X

FOREIGN PATENT DOCUMENTS

| 2932637 | 2/1981 | Fed. Rep. of Germany | 356/73.1 |
|---|---|---|---|
| WO82/02770 | 8/1982 | Int'lPat. Institute | 356/73.1 |
| 55-69033 | 5/1980 | Japan | 356/73.1 |
| 56-155828 | 12/1981 | Japan | 356/73.1 |
| 58-198015 | 11/1983 | Japan | 356/73.1 |

OTHER PUBLICATIONS

Ogoshi et al., "Optical Fibers", published Nov. 1976, published by Kabushikigaisha Ohmsha, p. 323, Methods for Measuring Defect Points and Loss Distribution.
"An Introduction to Optical Fiber", Allen H. Cherin, McGraw Hill International Book Company (1983), Chap. eight, Fiber Measurements, pp. 187–216, especially in pp. 196–201, the backscattering method is described.

Primary Examiner—Vincent P. McGraw
Attorney, Agent, or Firm—Cushman, Darby & Cushman

[57] ABSTRACT

Defects of infrared optical fibers during fabrication are inspected. The optical fiber runs from a fiber fabrication apparatus to a winding device. An integration sphere with a photodetector is placed at a point of the path of the running fiber. A light source shoots a light beam obliquely at the side surface of the running fiber or vertically at the beginning end of the fiber. Some portion of the light beam becomes propagating light. The defects of the fiber scatter the propagating light. The photodetector detects all the power of lights reflected within the diffuse reflective surface of the integration sphere. The output power of the photodetector is heightened to a higher level when a defect exists in the integration sphere, and the output power is lowered to a lower level when the defect exists between the outlet of the integration sphere and the light source. The position and extent of the defects are estimated by the change of the output power of the photodetector.

13 Claims, 3 Drawing Figures

METHOD FOR INSPECTING AN OPTICAL FIBER

BACKGROUND OF THE INVENTION

This invention relates to a method for inspecting an optical fiber to detect defects of the optical fiber at the time of fabrication.

Conventional methods for inspecting optical fibers—glassy optical fibers or crystalline optical fibers—can only be applied to separated optical fibers with both ends free. An inspecting light enters one free end and exits from the other free end of the optical fiber. When a light is introduced into one end of an optical fiber, the light propagates through the optical fiber to the other end. However if there are some defects in the optical fiber, some portions of the light scattered by the defects return to the incident end. The distance between the incident end and the defect spot can be calculated by the delay time of the back-scattered light.

Another conventional method of inspection is to introduce the inspecting lights from the side surfaces of optical fibers and to analyze the pattern of the forward-scattered light or the back-scattered light. The pattern of scattered light, which is defined as the power distribution of light along a diameter of an end surface of an optical fiber, represents the fluctuation of the refractive index of the optical fiber. The distribution of defects is known by the fluctuation of the refractive index.

The first conventional method is a suitable method to inspect the defects in optical fibers longer than tens of kilometers, and the second conventional method is an advantageous method to inspect a distribution of the refractive index of an optical fiber in detail. However, there has been no suitable method for inspecting defects of the optical fibers which have just been fabricated. The conventional methods require a detector and a light source to be placed at both free ends of the optical fiber, but the optical fiber which is being fabricated has only one end. The conventional method cannot be applied on the fiber without both free ends.

Glassy fibers now form a main current of optical fibers and have been greatly improved. However, crystalline fibers are being developed now. Crystalline fibers are subjected to occurrences of local defects on fabrication accidentally or inevitably.

Thus, an easy and reliable method for discovering local defects of optical fibers on fabrication has been desired earnestly.

SUMMARY OF THE INVENTION

A purpose of the invention is to provide a method for inspecting the existence of local defects of an optical fiber upon fabrication.

Another purpose of the invention is to provide a method for inspecting the local defects of an optical fiber with high resolution.

Yet another purpose of the invention is to provide a method for inspecting the local defects of an optical fiber in a short inspecting time.

This invention provides a method for inspecting continuously the local defects of an optical fiber upon fabrication. During fabrication, an optical fiber is continuously being drawn from a heated preform or a material melt. The optical fiber drawn from the fabrication apparatus is then wound by a winding device. The method of this invention inspects the existence of local defects of an optical fiber by passing a light through the fiber running from the fabrication apparatus to the winding device and by examining the existence of the scattering of the light in the fiber. For this purpose an integration sphere with a detector is mounted so as to enclose a portion of the running optical fiber. A light source which is at a distance from the integration sphere emits a strong light obliquely to the running optical fiber. Some portion of the emitted light penetrates into the fiber core. A portion of the light is scattered by some defects in the fiber core, and some portion of the scattered light propagates in the fiber core. This is the inspecting light. If some other defect exists in the propagating path of the fiber core, the defect scatters the inspecting light out of the fiber.

When the defect point is running in the integration sphere with a detector, the scattered light is emitted from the defect within the integration sphere. The detector mounted in the integration sphere detects all light powers which exist within the integration sphere. If the fiber has no defect within the integration sphere, a very small portion of the propagating light is emitted from the fiber core to the integration sphere. In this normal case the output power of the detector is small. On the other hand, the increase of the output power of the detector signifies that there are some defects in the portion of the fiber which exists within the integration sphere at the moment. Thus, this detecting device enables us to detect local defects with a high accuracy.

DETAILED DESCRIPTION OF THE EMBODIMENTS

Figure 1:
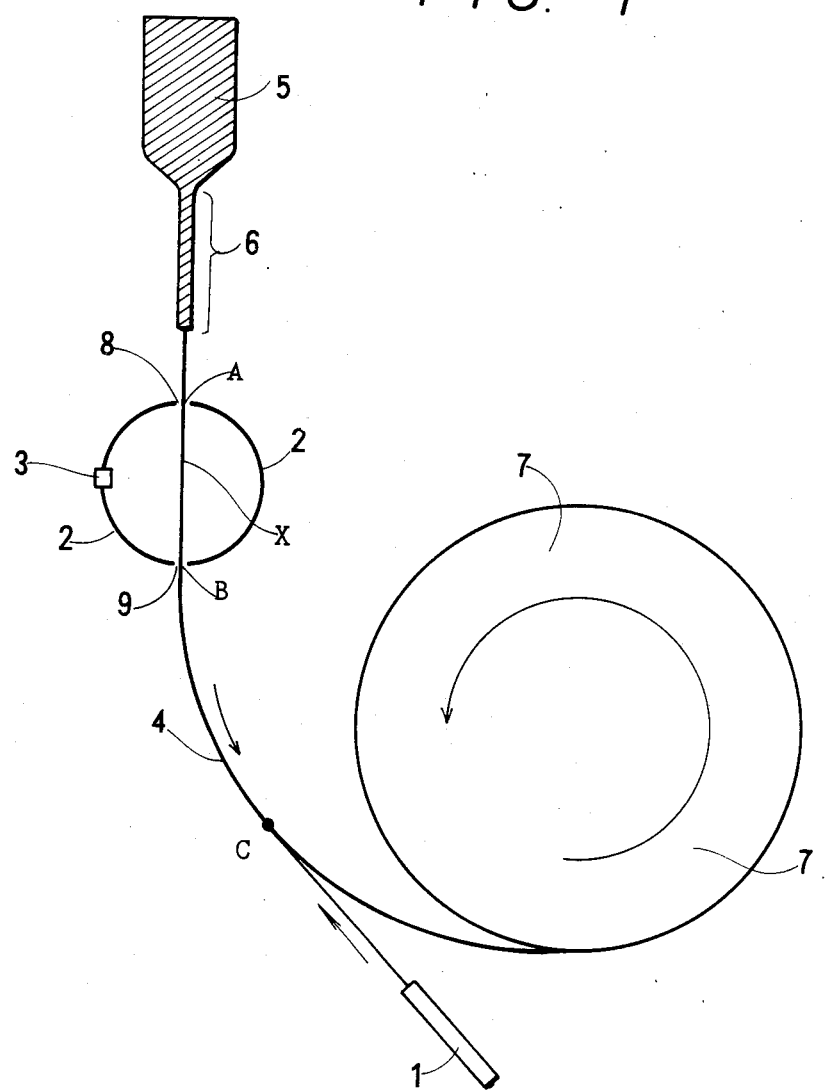
FIG. 1 is a schematic view of the apparatus for inspecting optical fibers as an embodiment of the invention.

In FIG. 1, a preform (5) is continuously being drawn into an optical fiber (4) by a fiber fabrication apparatus (6). The preform (5) is either a glassy preform or a crystalline preform. The fiber fabrication apparatus (6) is an extrusion machine in the case of the crystalline preform or a drawing machine in the case of the glassy preform. However, the preform (5) and the fiber fabrication apparatus (6) may be replaced by a material melt and a crystal growth apparatus in the case of crystalline fibers.

This invention relates to the inspecting of defects in infrared optical fibers. Thus, the crystalline fibers include three types of fibers—silver halides, thallium halides and alkali halides. Silver halides contain AgBr, AgCl and mixture crystals of AgBr and AgCl. Thallium halides contain TlBr, TlCl, TlI, and KRS-5 and KRS-6 (mixture of thallium halides). Alkali halides contain CsBr, CsI, NaCl and KCl. All these materials have high transparencies for infrared lights. Thus, the optical fibers fabricated from the materials can be used for the transmission of infrared light.

The glassy fibers mean chalcogenide glass fibers e.g. As-S, Ge-S, etc. The preform of the glassy fibers is of course, vitreous. A fiber is fabricated by drawing an end portion of the preform heated above the softening temperature. In the case of crystalline fibers—silver halides, on the other hand, thallium halides and alkali halides, two methods of fabrication are known. One is an extrusion method and the other a crystal growth method.

In the extrusion method a single-crystallized preform heated at a certain temperature is extruded into an optical fiber. Due to the mechanical stress at the extrusion, the optical fiber becomes not a single crystal, but a poly-crystal. The advantage of the extrusion method is the high speed of fabrication.

In the crystal growth method, a material melt in a crucible is heated above the melting point. A single-crystallized fiber is grown from the melt. Two methods are available. One is a pulling up method and another is a pulling down method. The pulling up method is only a version of a Czochralski method or an EFG method. A seed crystal with a diameter the same as the fiber is dipped and pulled up slowly. A single-crystallized fiber is thus drawn continously. In the pulling down method, on the other hand, the crucible has a small opening at its bottom, and the material melt is drained from the opening. The draining melt becomes a single-crystallized fiber. The speed of crystal growth in both methods is about several millimeters per minute. The advantage of the crystal growth method is the high quality of the fiber which is a single crystal with few defects.

These fabrication methods are well known. This invention may be applied to any fabrication method.

The optical fiber (4) drawn from the fiber fabrication apparatus (6) is wound at a constant speed by a winding device (7). A light source (1) which is placed between the fiber fabrication apparatus (6) and the winding device (7) shoots a light beam obliquely at the just-fabricated optical fiber (4). The light source is either a gas laser, a semiconductor laser or a lamp. A He-Ne laser is also available. The light source must emit a strong light beam. Because the light beam is launched obliquely against the fiber, some portion of the light beam is injected into the fiber and propagates in it.

The ground why the light beam is obliquely launched now will be explained. If the light beam was launched vertically into the fiber, the light beam would penetrate into the fiber more easily because the reflectivity is smaller. However, the vertical beam passes fully over the fiber and does not stay in the fiber core, despite its easy penetration. The vertical beam does not propagate in the fiber core unless some defects exist in the fiber core and they scatter the beam in the longitudinal direction. On the other hand, if the launching angle between the fiber axis and the beam axis is reduced from the right angle, the light power which is reflected at the fiber surface increases. In practice most of the light power is reflected at the fiber surface in the case of an oblique launching.

Small portions of the light power attains to the fiber core, but most of the light which once attains to the core does not stay in the fiber core as a propagating light because it passes out of the fiber. However, a very small portion of the light power can be converted into a propagating light due to a scattering by defects. Because the portion of light power which shall be converted into a propagating light is very small, however, a strong power light source is required.

If there was a perfect optical fiber with no loss, no light would leak out of the fiber core. No leakage from the core to the outer space signifies no effective injection of light from the outer space to the core according to the reciprocal principle of light propagation. However, all optical fibers fabricated by the methods mentioned above have some losses due to defects. Thus, the oblique launching may inject some portion of light as a propagating light into the core, because fiber cores inevitably have some defects. The light power scattered out of the core increases at a bending portion of the fiber. Thus it is more effective to form a bending portion of fiber and to launch the light into the bending portion.

An integration sphere (2) is placed at a point at a distance from the light source (1) in the running path of the optical fiber (4). The inner surface of the integration sphere (2) is a diffuse reflection surface. The integration sphere (2) has a small inlet (8) and a small outlet (9). The optical fiber (4) enters into the inner space of the integration sphere (2) through the inlet (8) and egresses through the outlet (9).

A photodetector (3) is mounted at a point of the inner surface of the integration sphere (2). All lights scattered from the light propagating in the fiber core shoot anywhere on the inner surface of the integration sphere and are reflected diffusely. After several reflections all the lights enter into the photodetector. Thus, the photodetector detects the sum of all light powers which have been generated in the integration sphere (2). The optical fiber (4) which has passed through the integration sphere (2) is then wound by the winding device (7).

The strong light beam emitted from the light source (1) must not enter into the integration sphere (2) through the outlet (9) or inlet (8) directly. Therefore, the integration sphere (2) must be at a distance from the light source (1), and the outlet (9) or the inlet (8) must deviate from the extension of the light beam emitted from the light source (1).

Figure 2:
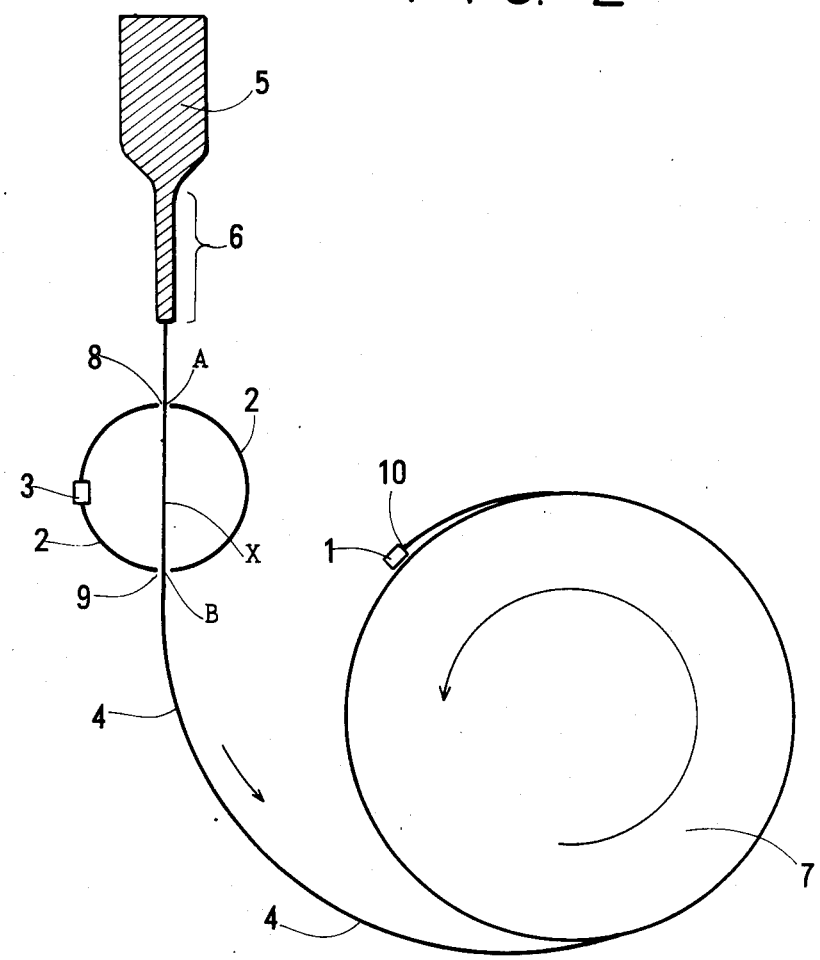
FIG. 2 is a schematic view of the apparatus for inspecting optical fibers as another embodiment of the invention.

FIG. 2 shows another embodiment in which a light source is placed in front of a winding end (10) of the optical fiber (4) instead of at point c as in FIG. 1. This disposition of the light source may be easily realized if the light source is small enough (such as a laser diode).

Because the light source (1) is mounted on the winding device which is rotating, the light source (1) is also rotating. However, it is easy to supply the electric power of the rotating light source, if it is a laser diode, because the required voltage is low.

In the second embodiment, the light source (1) can inject a large light power into the fiber core, because the light beam is vertical to the surface of the fiber end. This is an advantage of the second embodiment, for it is difficult to inject a light beam obliquely to the fiber core with a low loss. It is easy, however, to inject a light beam into a fiber through its end surface.

The functions of the inspection method now will be explained.

In FIG. 1, the position of the optical fiber which is passing through the inlet (8) is denoted by A. The position of the fiber passing through the outlet (9) is denoted by B. The distance between points A and B is equal to the length of the portion of fiber which exists in the integration sphere (2). The point at which the light beam emitted from the light source (1) shoots the optical fiber (4) is denoted by C. The optical fiber (4) passes the points A, B and C in succession.

A very small portion of a strong light beam emitted from the light source (1) is injected into the optical fiber as a propagating light at the point C. This propagating light. is called an inspecting light. The inspecting light propagates from the point C through the points B and A and reaches the preform (5). If the optical fiber (4) had no defects, the inspecting light would not leak from the optical fiber (4). Thus no light would be emitted within the integration sphere (2). However, if there are some defects in the optical fiber, the inspecting light is scattered at the defect points. Scattered lights can egress from the fiber core to the outer space, because the directions of scattered lights deviate from the direction of the core axis. The degree of the defects should be in proportion to the total power of the scattered lights.

The point of defect is denoted by X. When the defect point X stays before the inlet point A of the integration sphere (2), the scattering of the inspecting light occurs out of the integration sphere (2). Thus the light power which enters into the photodetector is very small. The detected light power is the small amount corresponding to the normal scattering (e.g. Rayleigh scattering).

Figure 3:
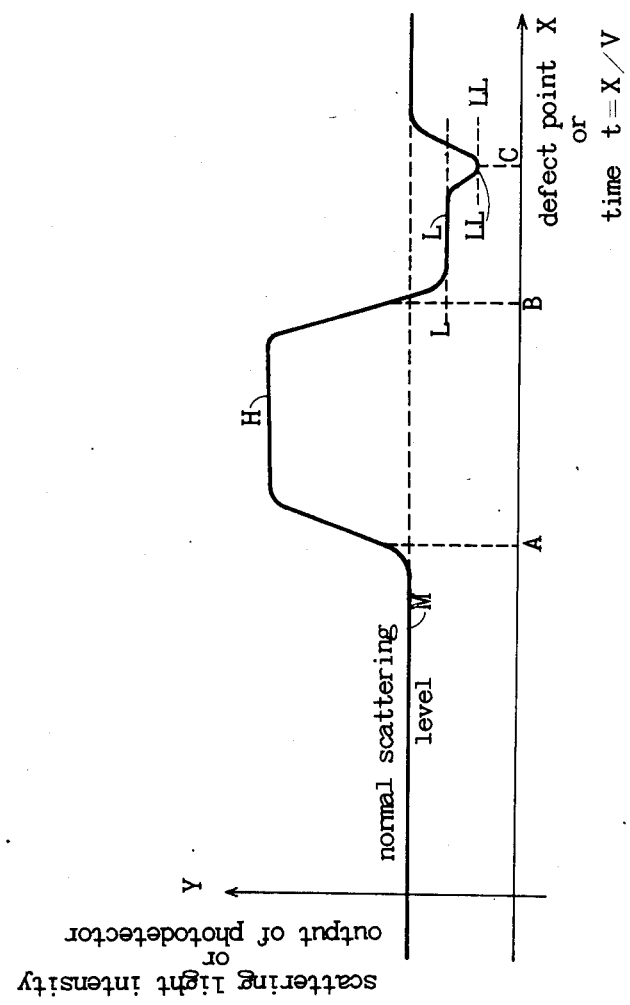
FIG. 3 is a graph of the change of the output Y of the detector as a function of the position X of defects.

FIG. 3 is a graph showing the output power Y of the photodetector as a function of the defect point X. The output power of the photodetector due to the normal scattering which occurs in a fiber without local defects is denoted by M. Before the defect point X reaches the point A, the output power Y of the detector is equal to M. When the defect point X reaches the point A, the output power Y rises to the level H. While te defect point X moves within the integration sphere, the higher level H is kept. Because the defect point X exists in the integration sphere, the lights scattered at X diffuse within the integration sphere and enter into the photodetector. Thus, the output power Y rises.

When the defect point X has passed the outlet point B, the defect point X exists between the integration sphere and the light source. The propagating light is scattered at the point X. Because of the scattering loss, the propagating light is reduced at X. Thus, the output power Y of the photodetector descends to the level L lower than the normal level M. Furthermore, when the defect point X reaches the light incident point C, the amount of injected light (leakage in) decreases. Thus, the output power Y of the photodetector is reduced to the bottom level LL lower than the lower level L. When the defect point X passes over the point C, the output power Y is restored to the normal level M.

The defect point can be detected by the appearance of the higher level H or the bottom level LL with a high accuracy, for when the higher level H is observed, we know there is a defect point between A and B. The accuracy of detection is determined by the diameter $\overline{AB}$ of the integration sphere. Thus, a smaller integration sphere heightens the accuracy of detection. Otherwise, when the bottom level LL is observed, we know a defect point X exists at the light incident point C.

The extent W of the defect may be estimated by the difference between the H level and the LL level or between the H level and the M level. Namely, the quantitative estimation of the extent W of the defect is given by:

$$W = H - LL \tag{1}$$

or $$W = H - M \tag{2}$$

The explanation above-mentioned is a static explanation.

In practice, because the optical fiber is being wound by the winding device, it is running at a constant speed V. In this case the abscissa X in FIG. 3 should be replaced by the product Vt, where V is the running speed and t is the time. Then the abscissa shall be deemed as a time axis. Thus, while the defect point X passes the point A, B and C, the output power Y of the photodetector takes the values M→H→L→LL→M with time.

On the assumption that the initial time $T_0$ for starting to wind the optical fiber and the running speed V of the fiber are already known, from the measured times $T_1$, $T_2$, ..., when the changes of the output power Y are observed, the points $X_1$, $X_2$, ..., at which some defects exist, are calculated by $$X_j = VT_j \quad (j = 1, 2, \ldots) \tag{3}$$

where j means integers which signify the number of defects.

In the embodiment shown in FIG. 2, in which a light source is placed in front of the starting end of the optical fiber on the winding device, the positions and extents of the defects can be estimated in a similar manner. However, there is no bottom level LL appearing in FIG. 3 in this case. The extents of the defects are estimated by the difference between the higher level H and the normal level M.

The advantages of the invention will be now explained.

(1) The positions and extents of the defects in an optical fiber can be detected in a quantitative manner by optical devices.

(2) The structure of the measuring system is simple.

(3) This method does not require any complicated data analysis like the measurement of the distribution of refractive index, because the change of the output power Y of the photodetector gives the value of the estimation of the defects by itself.

(4) This method enables us to inspect defects of an optical fiber continuously while its being fabricated. This is the most important advantage of this method.

(5) The resolving power can be raised to the order of several tens of centimeters, for the diameter of the integration sphere determines the resolving power. If a smaller integration sphere is used, the resolving power of the measurement is raised higher.

(6) This method is capable of high speed inspection. The response speed can be heightened to the intrinsic response speed of the photodetector.

What is claimed is:

1. A method for inspecting an optical fiber during fabrication, comprising the steps of:
   drawing said optical fiber from a fiber fabrication apparatus to a winding device through an integration sphere having an inlet opening, an outlet opening, an inner diffuse reflection surface, and a photodetector;
   shooting from a light source a strong beam of light obliquely at a side surface of said optical fiber such that a portion of the light beam penetrates into the fiber core and is scattered by defects in said core so as to form an inspecting light which propagates in said fiber core;
   measuring the light power detected by said photodetector within said integration sphere; and
   determining the position of a defect in said optical fiber by estimating the amount of change of output power of said photodetector as a function of time.

2. A method for inspecting an optical fiber as claimed in claim 1, wherein the optical fiber is a crystalline infrared fiber.

3. A method for inspecting an optical fiber as claimed in claim 2, wherein the crystalline infrared fiber is selected from the group consisting of alkali halides NaCl, KCl, CsI and CsBr.

4. A method for inspecting an optical fiber as claimed in claim 2, wherein the crystalline infrared fiber is selected from the group consisting of thallium halides TlBr, TlCl, TlI, KRS-5 and KRS-6.

5. A method for inspecting an optical fiber as claimed in claim 2, wherein the crystalline infrared fiber is selected from the group consisting of silver halides AgBr, AgCl, and mixture crystals of AgBr and AgCl.

6. A method for inspecting an optical fiber as claimed in claim 1, wherein the optical fiber is a glassy infrared fiber.

7. A method for inspecting an optical fiber as claimed in claim 6, wherein the glassy infrared fiber is selected from the group consisting of the chalcogenide glasses As-S and Ge-S.

8. A method for inspecting an optical fiber as claimed in claim 1, wherein the fiber fabrication apparatus is a drawing machine which draws the optical fiber from a heated glassy preform.

9. A method for inspecting an optical fiber as claimed in claim 1, wherein the fiber fabrication apparatus is an extruding machine which extrudes the optical fiber from a heated crystalline preform.

10. A method for inspecting an optical fiber as claimed in claim 1, wherein the fiber fabrication apparatus is a crystal growth apparatus which pulls up or pulls down a crystalline fiber from a material melt in a crucible.

11. A method for inspecting an optical fiber as claimed in claim 1, wheren the output power of said photodetector is at a high level H when said defect is within said integration sphere, at a medium level M during normal scattering, at a low level L when said defect is between said outlet opening and said light source, and at a lower level LL when said defect coincides with a light incident point of said light source on said optical fiber.

12. A method for inspecting an optical fiber as claimed in claim 11, including the further step of:
determining the extent of said defect in said optical fiber by estimating the difference between said high level H and said lower level LL.

13. A method for inspecting an optical fiber as claimed in claim 11, including the further step of:
determining the extent of said defect in said optical fiber by estimating the difference between said high level H and said medium level M.

* * * * *